United States Patent [19]

Haga et al.

[11] Patent Number: 4,912,225

[45] Date of Patent: Mar. 27, 1990

[54] BENZOTHIAZOLONES, AND THEIR PRODUCTION AND USE

[75] Inventors: Toru Haga, Takarazuka; Eiki Nagano, Tokyo; Ryo Sato; Kouichi Morita, both of Toyonaka, all of Japan

[73] Assignee: Sumitomo Chemical Company, Limited, Osaka, Japan

[21] Appl. No.: 253,034

[22] Filed: Oct. 4, 1988

Related U.S. Application Data

[62] Division of Ser. No. 89,172, Aug. 25, 1987, Pat. No. 4,824,465.

[30] Foreign Application Priority Data

Aug. 25, 1986 [JP]  Japan ................................. 61-198769

[51] Int. Cl.$^4$ ........................................... C07D 417/04
[52] U.S. Cl. ..................................................... 548/144
[58] Field of Search ............................................ 548/144

[56] References Cited

U.S. PATENT DOCUMENTS

| | | | |
|---|---|---|---|
| 3,069,429 | 12/1962 | Godson et al. | 548/144 |
| 3,741,977 | 6/1973 | Boesch | 548/144 |
| 3,846,439 | 11/1974 | Boesch et al. | 548/144 |
| 3,846,440 | 11/1974 | Boesch et al. | 548/144 |
| 4,562,190 | 12/1985 | Ueda et al. | 548/144 |
| 4,720,297 | 1/1988 | Haga et al. | 548/144 |

FOREIGN PATENT DOCUMENTS

| | | | |
|---|---|---|---|
| 0003619 | 8/1979 | European Pat. Off. | 548/144 |
| 2101938 | 7/1971 | Fed. Rep. of Germany | 548/144 |
| 1394774 | 7/1965 | France | 548/144 |
| 109578 | 6/1985 | Japan | 548/144 |

Primary Examiner—Robert Gerstl
Attorney, Agent, or Firm—Birch, Stewart, Kolasch & Birch

[57] ABSTRACT

A compound of the formula:

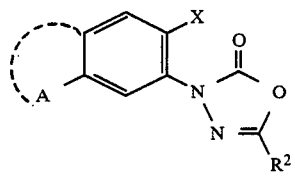

wherein A is a nitrogen-containing group selected from the group consisting of —NO$_2$, —NH$_2$, —N=C(NH$_2$)—S—, and —NH—CO—S—; X is a fluorine atom or a chlorine atom; and R$^2$ is a t-butyl group or a 1-methyl-cyclopropyl group. These compounds are useful as intermediates in the production of herbicidal benzothiazolone compounds.

7 Claims, No Drawings

BENZOTHIAZOLONES, AND THEIR PRODUCTION AND USE

This application is a divisional of copending application Ser. No. 07/089,172, filed on Aug. 25, 1987 now U.S. Patent No. 4,824,485.

The present invention relates to benzothiazolones, and their production and use. More particularly, the invention relates to novel benzothiazolones, a process for producing them, and their use as herbicides.

Certain benzothiazolone derivatives such as 4-chloro-2,3-dihydro-2-oxobenzothiazol-3-ylacetic acid (benazolin) [Herbicide Handbook of the Weed Science Society of America, 5th Ed., p. 40 (1983)] are known to be effective as herbicides. However their herbicidal activity is not necessarily satisfactory.

It has now been found that the benzothiazolones of the formula:

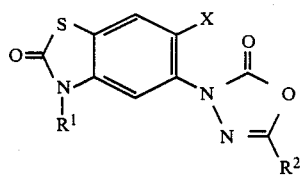

(I)

wherein $R^1$ is a $C_1$–$C_5$ alkyl group, a $C_3$–$C_4$ alkenyl group, a $C_3$–$C_4$ alkynyl group or a $C_1$–$C_2$ alkoxy($C_1$–$C_2$)alkyl group, $R^2$ is a t-butyl group or a 1-methylcyclopropyl group and X is a fluorine atom or a chlorine atom exhibit a high herbicidal activity against a wide variety of weeds including broad-leaved weeds, Graminaceous weeds, Commelinaceous weeds and Cyperaceous weeds in agricultural plowed fields by foliar or soil treatments without producing any material phytotoxicity on various agricultural crops such as corn, wheat, rice plant, soybean and cotton. Examples of the broad-leaved weeds include wild buckwheat (*Polygonum convolvulus*), pale smartweed (*Polygonum lapathifolium*) common purslane . (*Portulaca oleracea*), common chickweed (*Stellaria media*), common lambsquarters (*Chenopodium album*), redroot pigweed (*Amaranthus retroflexus*),radish (*Raphanus sativus*), wild mustard (*Sinapis arvensis*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), tall morningglory (*Ipomoea purpurea*), field bindweed (*Convolvulus arvensis*), jimsonweed (*Datura stramonium*), black nightshade (*Solanum nigrum*), persian speedwell (*Veronica persica*), common cocklebur (*Xanthium pensylvanicum*), scentless chamomile (*Matricaria perforata*), etc. Examples of Graminaceous weeds include Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), etc. Examples of the Commelinaceous weeds include asiatic dayflower (*Commelina communis*), etc.

The benzothiazolones (I) of the invention are also effective in exterminating paddy field weeds including Graminaceous weeds such as barnyardgrass (*Echinochloa oryzicola*), broad-leaved weeds such as common falsepimpernel (*Lindernia procumbens*), indian toothcup (*Rotala indica*) and waterwort (*Elatine triandra*), Cyperaceous weeds such as hardstem bulrush (*Scirpur juncoides*) and needle spikerush (*Eleocharis acicularis*) and others such as monochoria (*Monochoria vaginalis*) and arrowhead (*Sagittaria pygmaea*) without producing any phytotoxicity to rice plants on flooding treatment.

Among the benzothiazolones (I), preferred are those wherein $R^2$ is a t-butyl group. More preferred are those wherein $R^1$ is a $C_1$–$C_4$ alkyl group, a $C_3$–$C_4$ alkenyl group, a $C_3$–$C_4$ alkynyl group or a $C_1$–$C_2$ alkoxymethyl group. Still more preferred are those wherein $R^1$ is a $C_1$–$C_3$ alkyl group, a $C_3$–$C_4$ alkenyl group or a $C_3$–$C_4$ alkynyl group. The most preferred are those wherein $R^1$ is a $C_3$–$C_4$ alkenyl group or a $C_3$–$C_4$ alkynyl group. Typical examples of the preferred compounds are 3-[6-fluoro-3-(2-propenyl)-2(3H)-benzothiazolon -5-yl]-5-(1,1-dimethylethyl)-1,3,4-oxadiazol-2(3H)-one, 3-[6-fluoro-3-(2-propynyl)-2(3H)-benzothiazolon-5-yl]-5-(1,1-dimethylethyl) -2(3H)-benzothiazolon-5-yl]-5-(1,1-dimethyl-ethyl) -1,3,4-oxadiazol-2(3H)-one, 3-[6-chloro-3-(2-propynyl) -2(3H)-benzothiazolon-5-yl]-5-(1,1-dimethylethyl)-1,3,4-oxadiazol -2(3H)-one, etc.

The benzothiazolones (I) of the present invention are prepared by reacting a compound of the formula:

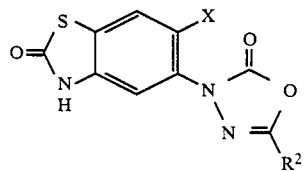

(II)

wherein $R^2$ and X are each as defined above with a compound of the formula:

$R^1$—Y (III)

wherein $R^1$ is as defined above and Y is an acid-forming reactive group such as a chlorine atom, a bromine atom, an iodine atom, a methanesulfonyl group or a p-toluenesulfonyl group, usually in a solvent at a temperature of about 0° to 100° C. for a period of about 0.5 to 48 hours in the presence of a base.

The compound (III) and the base may be respectively used in amounts of about 1.0 to 10 equivalents and of about 1.0 to 10 equivalents to the compound (II). As the solvent, there may be used aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), nitriles (e.g. acetonitrile, isobutylonitrile), acid amides (e.g. formamide, N,N dimethylformamide, acetamide), sulfur compounds (e.g. dimethylsulfoxide, sulphorane), water, etc. These may be used solely or in combination. Examples of the base are inorganic bases (e.g. sodium hydroxide, potassium hydroxide, sodium carbonate, potassium carbonate, sodium hydride), alkali metal alkoxides (e.g. sodium methoxide, sodium ethoxide), etc.

After completion of the reaction, the reaction mixture is subjected to an ordinary post-treatment such as extraction with an organic solvent and concentration. If desired, any conventional purification procedure such as chromatography or recrystallization may be adopted.

Typical examples of the benzothiazolones (I) which may be produced through the above procedure are shown in Table 1.

TABLE 1

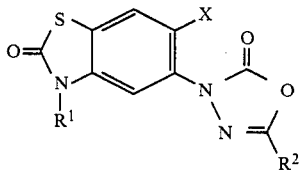

(I)

| X | R¹ | R² |
|---|---|---|
| F | CH₃ | t-C₄H₉ |
| F | C₂H₅ | t-C₄H₉ |
| F | n-C₃H₇ | t-C₄H₉ |
| F | i-C₃H₇ | t-C₄H₉ |
| F | n-C₄H₉ | t-C₄H₉ |
| F | i-C₄H₉ | t-C₄H₉ |
| F | sec-C₄H₉ | t-C₄H₉ |
| F | n-C₅H₁₁ | t-C₄H₉ |
| F | i-C₅H₁₁ | t-C₄H₉ |
| F | (C₂H₅)₂CH— | t-C₄H₉ |
| F | CH₂=CHCH₂— | t-C₄H₉ |
| F | CH₃CH=CHCH₂— | t-C₄H₉ |
| F | CH₂=C(CH₃)—CH₂— | t-C₄H₉ |
| F | CH₂=CH—CH(CH₃)— | t-C₄H₉ |
| F | CH≡CCH₂— | t-C₄H₉ |
| F | CH₃C≡CCH₂— | t-C₄H₉ |
| F | CH≡C—CH(CH₃)— | t-C₄H₉ |
| F | CH₃OCH₂ | t-C₄H₉ |
| F | C₂H₅OCH₂ | t-C₄H₉ |
| F | CH₃OCH(CH₃)— | t-C₄H₉ |
| Cl | CH₃ | t-C₄H₉ |
| Cl | C₂H₅ | t-C₄H₉ |
| Cl | n-C₃H₇ | t-C₄H₉ |
| Cl | i-C₃H₇ | t-C₄H₉ |
| Cl | n-C₄H₉ | t-C₄H₉ |
| Cl | i-C₄H₉ | t-C₄H₉ |
| Cl | sec-C₄H₉ | t-C₄H₉ |
| Cl | n-C₅H₁₁ | t-C₄H₉ |
| Cl | i-C₅H₁₁ | t-C₄H₉ |
| Cl | (C₂H₅)₂CH— | t-C₄H₉ |
| Cl | CH₂=CHCH₂— | t-C₄H₉ |
| Cl | CH₃CH=CHCH₂— | t-C₄H₉ |
| Cl | CH₂=C(CH₃)—CH₂— | t-C₄H₉ |
| Cl | CH₂=CH—CH(CH₃)— | t-C₄H₉ |
| Cl | CH≡CCH₂— | t-C₄H₉ |
| Cl | CH₃C≡CCH₂— | t-C₄H₉ |
| Cl | CH≡C—CH(CH₃)— | t-C₄H₉ |
| Cl | CH₃OCH₂ | t-C₄H₉ |
| Cl | C₂H₅OCH₂ | t-C₄H₉ |

TABLE 1-continued

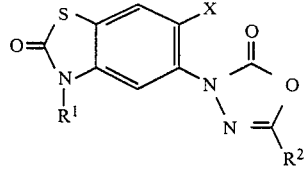

(I)

| X | R¹ | R² |
|---|---|---|
| Cl | CH₃OCH(CH₃)— | t-C₄H₉ |
| F | CH₃ | 1-methylcyclopropyl |
| F | C₂H₅ | 1-methylcyclopropyl |
| F | n-C₃H₇ | 1-methylcyclopropyl |
| F | i-C₃H₇ | 1-methylcyclopropyl |
| F | n-C₄H₉ | 1-methylcyclopropyl |
| F | i-C₄H₉ | 1-methylcyclopropyl |
| F | sec-C₄H₉ | 1-methylcyclopropyl |
| F | n-C₅H₁₁ | 1-methylcyclopropyl |
| F | i-C₅H₁₁ | 1-methylcyclopropyl |

TABLE 1-continued

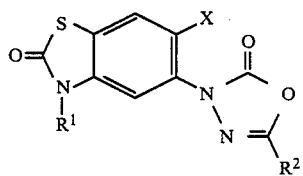

(I)

| X | R¹ | R² |
|---|---|---|
| F | $(C_2H_5)_2CH-$ | cyclopropyl-CH₃ |
| F | $CH_2=CHCH_2-$ | cyclopropyl-CH₃ |
| F | $CH_3CH=CHCH_2-$ | cyclopropyl-CH₃ |
| F | $CH_2=C(CH_3)-$ | cyclopropyl-CH₃ |
| F | $CH_2=CH-CH(CH_3)-$ | cyclopropyl-CH₃ |
| F | $CH\equiv CCH_2-$ | cyclopropyl-CH₃ |
| F | $CH_3C\equiv CCH_2-$ | cyclopropyl-CH₃ |
| F | $CH\equiv C-CH(CH_3)-$ | cyclopropyl-CH₃ |
| F | $CH_3OCH_2$ | cyclopropyl-CH₃ |
| F | $C_2H_5OCH_2$ | cyclopropyl-CH₃ |

TABLE 1-continued

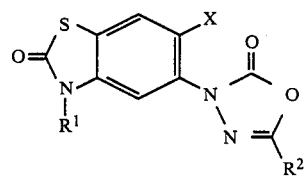

(I)

| X | R¹ | R² |
|---|---|---|
| F | $CH_3OCH(CH_3)-$ | cyclopropyl-CH₃ |
| Cl | $CH_3$ | cyclopropyl-CH₃ |
| Cl | $C_2H_5$ | cyclopropyl-CH₃ |
| Cl | $n-C_3H_7$ | cyclopropyl-CH₃ |
| Cl | $i-C_3H_7$ | cyclopropyl-CH₃ |
| Cl | $n-C_4H_9$ | cyclopropyl-CH₃ |
| Cl | $i-C_4H_9$ | cyclopropyl-CH₃ |
| Cl | $sec-C_4H_9$ | cyclopropyl-CH₃ |
| Cl | $n-C_5H_{11}$ | cyclopropyl-CH₃ |
| Cl | $i-C_5H_{11}$ | cyclopropyl-CH₃ |

TABLE 1-continued (I) Structure: benzothiazolone with S, N-R¹, C=O, X substituent, connected to N-N=C(R²)-O-C(=O) oxadiazolone ring

| X | R¹ | R² |
|---|----|----|
| Cl | (C₂H₅)₂CH— | ![cyclopropyl-CH₃] |
| Cl | CH₃OCH(CH₃)— | ![cyclopropyl-CH₃] |
| Cl | CH₂=CHCH₂— | ![cyclopropyl-CH₃] |
| Cl | CH₃CH=CHCH₂— | ![cyclopropyl-CH₃] |
| Cl | CH₂=C(CH₃)— | ![cyclopropyl-CH₃] |
| Cl | CH₂=CH—CH(CH₃)— | ![cyclopropyl-CH₃] |
| Cl | CH≡CCH₂— | ![cyclopropyl-CH₃] |
| Cl | CH₃≡CCH₂— | ![cyclopropyl-CH₃] |
| Cl | CH≡C—CH(CH₃)— | ![cyclopropyl-CH₃] |
| Cl | CH₃OCH₂ | ![cyclopropyl-CH₃] |

TABLE 1-continued

| X | R¹ | R² |
|---|----|----|
| Cl | C₂H₅OCH₂ | ![cyclopropyl-CH₃] |

A typical embodiment of the invention for production of the benzothiazolones (I) is illustratively shown in the following Example.

EXAMPLE 1

A dispersion of sodium hydride (50% oil; 0.16 g) in dry N,N-dimethylformamide (3 ml) was cooled to 0° C., and a solution of 3-[6-chloro-2(3H)-benzothiazolon-5-yl]-5-(1,1-dimethylethyl) -1,3,4-oxadiazol-2(3H)-one (1.00 g) in dry N,N-dimethylformamide (3 ml) was dropwise added thereto at the same temperature, followed by stirring at the same temperature for 30 minutes. Upon addition of propargyl bromide (0.44 g), the resultant mixture was heated to 50° C. and stirred for 5 hours. The reaction mixture was allowed to cool, combined with water and extracted with ethyl acetate. The extract was washed with water, dried and concentrated. The residue was purified by silica gel thin layer chromatography with a mixture of ether and hexane (1 : 1) as an eluent to give 3-[6-chloro-3-(2-propenyl)-2(3H)-benzothiazolon-5-yl] -5-(1,1-dimethylethyl)-1,3,4-oxadiazol -2(3H)-one (0.28 g). $n_D^{25.5}$ 1.5703.

In the same manner as above, the benzothiazolones (I) as shown in Table 2 were prepared.

TABLE 2

| Compound No. | X | R¹ | R² | Physical property |
|---|---|----|----|-------|
| 1 | F | CH₃CH₂— | t-C₄H₉ | m.p. 133–134° C. |
| 2 | F | i-C₃H₇— | t-C₄H₉ | m.p. 162.3° C. |
| 3 | F | CH₃(C₂H₅)CH— | t-C₄H₉ | $n_D^{22.5}$ 1.5440 |
| 4 | F | (C₂H₅)₂CH— | t-C₄H₉ | $n_D^{23.5}$ 1.5625 |
| 5 | F | CH₂=CHCH₂— | t-C₄H₉ | $n_D^{24.5}$ 1.5602 |
| 6 | F | CH≡CCH₂— | t-C₄H₉ | $n_D^{24.5}$ 1.5565 |
| 7 | F | i-C₃H₇ | 1-methylcyclopropyl | m.p. 119.3° C. |

TABLE 2-continued

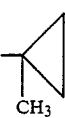
(I)

| Compound No. | X | R¹ | R² | Physical property |
|---|---|---|---|---|
| 8 | Cl | $CH_3CH_2-$ | $t-C_4H_9$ | $n_D^{25.5}$ 1.5694 |
| 9 | Cl | $CH_3CH_2CH_2-$ | $t-C_4H_9$ | $n_D^{25.5}$ 1.5670 |
| 10 | Cl | $CH_2CHCH_2-$ | $t-C_4H_9$ | $n_D^{25.5}$ 1.5800 |
| 11 | Cl | $CH\equiv CCH_2$ | $t-C_4H_9$ | $n_D^{25.5}$ 1.5703 |
| 12 | Cl | $CH_3OCH_2-$ | $t-C_4H_9$ | m.p. 69–70° C. |
| 13 | Cl | $CH\equiv CCH_2-$ | cyclopropyl-CH₃ | $n_D^{27.0}$ 1.5842 |

The starting compound (II) in the process of this invention may be produced according to the following scheme:

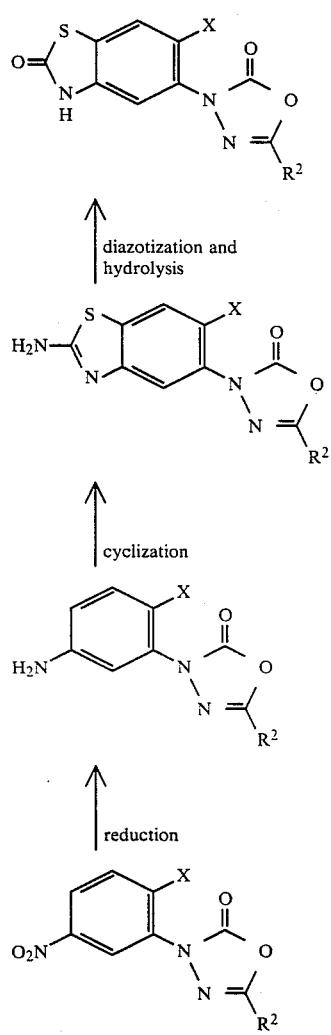

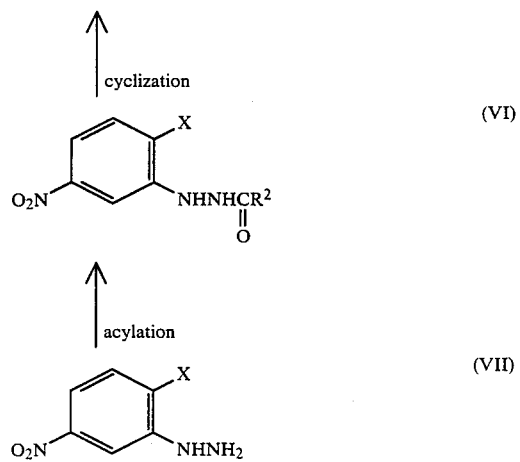

wherein X and R² are each as defined above.

Each reaction as set forth above will be hereinafter explained in detail.

(1) Production of the compound (II) from the compound (III):

The compound (II) may be prepared by treating the compound (III) with a diazotizing agent such as alkali metal nitrite (e.g. sodium nitrite, potassium nitrite) in a solvent (e.g. sulfuric acid, hydrochloric acid) at a temperature of about -5 to 5 ° C. for a period of about 0.5 to 24 hours, followed by hydrolysis of the resultant diazo compound at a temperature of about 70° to 100° C. for a period of about 0.5 to 24 hours. In the reaction, the diazotizing agent is used in an amount of about 1 to 2 equivalents to the compound (III).

After completion of the reaction, the reaction mixture is diluted with water, extracted with an organic solvent and concentrated. The residue is subjected to a conventional post-treatment such as washing with water, drying and concentration. When desired, any purification method such as chromatography may be applied.

A typical example for production of the compound (II) is illustratively shown in the following Example.

EXAMPLE 2

3-(2-Amino-6-chlorobenzothiazol-5-yl)-5-(1,1-dimethylethyl) -1,3,4-oxadiazol-2(3H)one (39.6 g) was dissolved in a mixture of 50% sulfuric acid (234.3 ml) and 1,4-dioxane (234.3 ml) and cooled to 0° C.. An aqueous solution of sodium nitrite (8.39 g) was dropwise added thereto at 0° to 5° C., followed by stirring at 0° to 5° C. for 20 minutes to afford a diazonuum solution. Separately, a mixture of water (79.6 ml) and conc. sulfuric acid (116.8 ml) was heated under reflux, and the above obtained diazonium solution was dropwise added thereto. After evolution of nitrogen gas, the reaction mixture was allowed to cool, combined with water and extracted with ethyl acetate. The extract was washed with water, dried and distilled under reduced pressure to give 3-[6-chloro-2(3H) -benzothiazolon-5-yl]-5-(1,1-dimethylethyl)-1,3,4-oxadiazol-2(3H)-one (8.63 g) as a resinous substance.

¹H-NMR δ (CDCl₃+DMSO-d₆): 1.22 (s, 9H), 6.4–7.5 (m, 2H), 8.2–8.7 (brs, 1H).

In the same manner as above, the compounds (II) as shown in Table 3 were prepared:

TABLE 3

Structure (II): benzothiazol-2(3H)-one fused ring with X substituent and N-N=C(R²)- acetate group

| X | R² | Physical property |
|---|----|-------------------|
| F | t-C₄H₉ | ¹H—NMR δ (CDCl₃ + DMSO-d₆): 1.37 (s,9H), 6.0–7.0 (brs,1H), 7.29 (d,1H), 7.42 (d,1H) |
| F | cyclopropyl-CH₃ | ¹H—NMR δ (CDCl₃ + DMSO-d₆): 0.7–1.1 (m,2H), 1.1–1.4 (m, 2H), 1.46 (s,3H), 7.28 (d, 1H), 7.76 (d,1H) |
| Cl | t-C₄H₉ | ¹H—NMR δ (CDCl₃ + DMSO-d₆): 1.22 (s,9H), 6.4–7.5 (m, 2H), 8.2–8.7 (brs,1H) |
| Cl | cyclopropyl-CH₃ | m.p., 220.5° C. |

(2) Production of the compound (III) from the compound (IV):

The compound (III) may be produced by reacting the compound (IV) with a thiocyanate (e.g. sodium thiocyanate, ammonium thiocyanate, potassium thiocyanate) and then with halogen (e.g. bromine, chlorine) in a solvent (e.g. aqueous acetic acid, aqueous hydrochloric acid, aqueous sulfuric acid) at a temperature of about 0° to 50° C. for a period of about 1 to 100 hours. In the reaction, the thiocyanate and the halogen are used respectively in amounts of about 1 to 10 equivalents and of about 1 to 10 equivalents to the compound (IV).

After completion of the reaction, the reaction mixture is neutralized and extracted with an organic solvent, followed, by concentration. The residue is subjected to a conventional post-treatment such as washing with water, drying and concentration. If necessary, any purification method such as chromatography may be applied.

A typical example for production of the compound (III) is illustratively shown in the following Example.

EXAMPLE 3

3-(5-Amino-2-chlorophenyl)-5-(1,1-dimethyl-ethyl)-1,3,4-oxadiazol-2(3H)-one (38.28 g) was dissolved in 95% acetic acid (138.20 g), and ammonium thiocyanate (27.64 g) was added thereto, followed by stirring at room temperature for 3 hours. To the resultant mixture, a solution of bromine (27.64 g) in acetic acid (41.46 g) was added, followed by stirring at room temperature for 12 hours. The reaction mixture was combined with hot water (274.7 ml), heated to 100° C. and filtered while hot. The filtrate was neutralized with sodium carbonate and extracted with ethyl acetate. The extract was washed with water, dried and distilled under reduced pressure to give 3-(2-amino-6-chloro-benzothiazol -5-yl)-5-(1,1-dimethylethyl)-1,3,4-oxadiazol-2(3H)-one (39.06 g) as a resinous substance.

¹H-NMR δ (CDCl₃+DMSO-d₆): 1.22 (s, 9H), 5.0–5.5 (brs, 2H), 6.9–7.8 (m, 2H).

In the same manner as above, the compounds (III) as shown in Table 4 were prepared:

TABLE 4

Structure (III): 2-amino-benzothiazole fused ring with X substituent and N-N=C(R²)- acetate group

| X | R² | Physical property |
|---|----|-------------------|
| F | t-C₄H₉ | ¹H—NMR δ (CDCl₃ + DMSO-d₆): 1.35 (s,1H), 6.7–7.2 (brs,2H), 7.33 (d,1H), 7.46 (d,1H) |
| F | cyclopropyl-CH₃ | ¹H—NMR δ (CDCl₃ + DMSO-d₆): 0.90 (m,2H), 1.25 (m,2H), 1.40 (s,3H), 6.8–7.4 (brs, 2H), 7.32 (d,1H), 7.46 (d,1H) |
| Cl | t-C₄H₉ | ¹H—NMR δ (CDCl₃ + DMSO-d₆): 1.33 (s,9H), 5.0–5.5 (brs, 2H), 6.9–7.8 (m,2H) |
| Cl | cyclopropyl-CH₃ | ¹H—NMR δ (CDCl₃ + DMSO-d₆): 0.95 (m,2H), 1.30 (m,2H), 1.45 (s,3H), 2.9–3.5 (brs, 2H), 7.0–7.8 (m,2H) |

(3) Production of the compound (IV) from the compound (V):

The compound (IV) may be prepared by treating the compound (V) with a reducing agent (e.g. iron powder, zinc powder, tin powder, zinc chloride, stannous chloride) in an aqueous medium (e.g. acetic acid, chloric acid, sulfuric acid), if necessary, comprising an organic solvent (e.g. ethyl acetate, methyl isobutyl ketone) at a temperature of about 60° to 120° C. for a period of about 1 to 24 hours. In the case of using iron powder, a catalyst (e.g. ferrous chloride, ferric chloride) usually coexists in the reaction system. The reducing agent is used in an amount of 2.25 to 30 equivalents to the compound (V).

After completion of the reaction, the reaction mixture is filtered, and the filtrate is extracted with an organic solvent. The extract is washed with water and a sodium bicarbonate solution and then concentrated to give the compound (IV). I necessary, any purification method such as recrystallization or chromatography may be applied to the product.

A typical example for production of the compound (IV) is illustratively shown in the following Example.

EXAMPLE 4

Electrolytic iron powder (93.5 g) was suspended in 5% acetic acid (187.2 ml), and the suspension was heated to 80° C.. A solution of 3-(2-chloro-5-nitrophenyl)-5-(1,1-dimethylethyl) -1,3,4-oxadiazol-2(3H)-one (47.21 g) in acetic acid (167.5 ml) and ethyl acetate (167.5 ml) was added thereto. The resultant mixture was heated at a temperature of 70° C. for 3 hours. The reaction mixture was subjected to filtration on celite while hot. The filtrate was extracted with ethyl acetate, and the extract was washed with water and sodium bicarbonate solution and dried. Removal of the solvent under reduced pressure gave 3-(5-amino-2-chlorophenyl) -5-(1,1-dimethylethyl)-1,3,4-oxadiazol-2(3H)-one (38.28 g). m.p., 126.0° C..

In the same manner as above, the compounds (IV) as shown in Table 5 were prepared:

TABLE 5

(IV) [structure: H2N-phenyl-X with oxadiazolone ring bearing R²]

| X | R² | Physical property |
|---|---|---|
| F | t-C₄H₉ | ¹H—NMR δ (CDCl₃ + DMSO-d₆): 1.33 (s,9H), 3.88 (s,3H), 6.47–7.3 (m,3H) |
| F | cyclopropyl-CH₃ | m.p. 110.1° C. |
| Cl | t-C₄H₉ | m.p. 126.0° C. |
| Cl | cyclopropyl-CH₃ | m.p. 138.3° C. |

(4) Production of the compound (V) from the compound (VI):

The compound (V) may be produced by reacting the compound (VI) with phosgene, followed by treatment with an organic base (e.g. triethylamine, tributylamine, diisopropylethylamine, N,N-diethylaniline, pyridine, picoline, proton sponge) in a solvent such as a hydrocarbon (e.g. benzene, toluene, xylene), a halogenated hydrocarbon (e.g. dichloromethane, chloroform, 1,2-dichloroethane, 1,1,1-trichloroethane) or their mixtures at a temperature of about 0° to 150° C. for a period of about 1 to 100 hours. In the reaction, phosgene and the base are respectively used in amounts of about 1 to 10 equivalents and of about 1 to 5 equivalents to the compound (VI).

Recovery of the compound (V) can be performed by addition of water to the reaction mixture, extracting the resultant mixture with an organic solvent, washing the extract with water, followed by drying and concentrating. When desired, any purification procedure such as recrystallization or chromatography may be adopted.

A typical example for production of the compound (V) is illustratively shown in the following Example.

EXAMPLE 5

A toluene solution of phosgene prepared by adding active carbon and toluene (500 ml) to trichloromethyl chlorocarbonate (82.5 g) was added to 1-(2-chloro-5-nitrophenyl) -2-(2,2-dimethylpropionyl)hydrazine (42.23 g), and the resultant mixture was heated under reflux for 2 hours. Active carbon was further added thereto, and heating under reflux was continued for 15 hours. After removal of active carbon by filtration, the filtrate was concentrated. To the concentrated solution, a solution of triethylamine (23.54 g) in toluene (155 ml) was added, and the resulting mixture was stirred at room temperature for 12 hours. The reaction mixture was combined with water. The toluene layer was separated, washed with water, dried and concentrated under reduced pressure to give 3-(2-chloro-5-nitrophenyl)-5-(1,1-dimethylethyl) -1,3,4-oxadiazol-2(3H)-one (47.51 g). m.p., 130.4° C..

In the same manner as above, the compounds (V) as shown in Table 6 were prepared.

TABLE 6

(V) [structure: O2N-phenyl-X with oxadiazolone ring bearing R²]

| X | R² | Physical property |
|---|---|---|
| F | t-C₄H₉ | m.p. 89.8° C. |
| F | cyclopropyl-CH₃ | ¹H—NMR δ (CDCl₃ + DMSO-d₆): 0.7–1.1 (m,2H), 1.1–1.4 (m, 2H), 1.45 (s,3H), 7.34 (t, 1H), 8.05–8.55 (m,2H) |
| Cl | t-C₄H₉ | m.p. 130.4° C. |
| Cl | cyclopropyl-CH₃ | m.p. 99.7° C. |

(5) Production of the compound (VI) from the compound (VII):

The compound (VI) may be prepared by treating the compound (VII) with an acylating agent such as a carboxylic chloride or a carboxylic anhydride in the presence or absence of an organic base (e.g. triethylamine, tributylamine, diisopropylethylamine, N,N-dimethylaniline, N,N-diethylaniline, pyridine, picoline, proton sponge) in an organic solvent such as a hydrocarbon (e.g. dichloromethane, chloroform, 1,2-dichloroethane, 1,1,1-trichloroethane), an ether (e.g. diethyl ether, diisopropyl ether, tetrahydrofuran, 1,4-dioxane, ethylene glycol dimethyl ether) or their mixture at a temperature of about −10 to 150° C. for a period of about 1 to 100 hours. In the reaction, the acylating agent and the base may be used respectively in amounts of about 1 to 5 equivalents and of about 1 to 5 equivalents to the compound (VII).

Recovery of the compound (VI) can be accomplished by adding water to the reaction mixture, extracting the resultant mixture with an organic solvent, washing the extract with water, followed by drying and concentrating. When desired, any purification procedure such as recrystallization or chromatography may be adopted.

A typical example for production of the compound (VI) is illustratively shown in the following Example.

EXAMPLE 6

To a solution of 2-chloro-5-nitrophenylhydrazine (37.60 g) in dichloromethane (200 ml), triethylamine (22.27 g) and pivaloyl chloride (26.59 g) were added, and the resultant mixture was stirred at room temperature for 12 hours. The reaction mixture was combined with water. The dichloromethane layer was washed with water, dried and concentrated under reduced pressure to give 1-(2-chloro-5-nitrophenyl)-2-(2,2-dimethylpropionyl)hydrazine (42.23 g). m.p., 153.3° C..

In the same manner as above, the compounds (VI) as shown in Table 7 were prepared.

TABLE 7

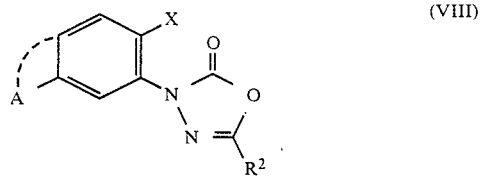

| X | R² | Physical property |
|---|----|-------------------|
| F | t-C₄H₉ | m.p. 142.7° C. |
| F | ![cyclopropyl-CH3] | ¹H—NMR δ (CDCl₃ + DMSO-d₆): 0.45–1.0 (m,2H), 1.0–1.4 (m, 2H), 1.40 (s,3H), 5.9–6.2 (brs,1H), 6.53–7.3 (m,1H), 7.5–7.85 (m,2H), 7.85–8.2 (brs,1H) |
| Cl | t-C₄H₉ | m.p. 153.3° C. |
| Cl | ![cyclopropyl-CH3] | m.p. 137.7° C. |

2-fluoro or chloro-5-nitrophenylhydrazine as the starting material can be produced from 2fluoro or chloro-5-nitroaniline according to the method as described in J.Chem.Soc., (C), 1970, 2106.

The above intermediate compounds, i.e. the compounds (II), (III), (IV) and (V), are novel and can be represented by the general formula:

(VIII)

wherein A is a nitrogen-containing group chosen from $-NO_2$, $-NH_2$, $-N=C(NH_2)-S-$ and $-NH-CO-S-$ and X and $R^2$ are each as defined above. When A represents $-NO_2$ or $-NH_2$, the linkage indicated by the dotted line does not exist. When A represents $-N=C(NH_2)-S-$ or $-NH-CO-S-$, the linkage indicated by the dotted line corresponds to the bonding between the sulfur atom in the group represented by A and the carbon atom in the benzene ring.

For the practical use of the benzothiazolone (I), they are usually formulated with conventional solid or liquid carriers or diluents as well as surface active agents or auxiliary agents into conventional preparation forms such as emulsifiable concentrates, wettable powders, suspensions and granules. The content of the benzothiazolone (I) as the active ingredient in such preparation forms is usually within a range of about 0.1 to 80% by weight, preferably of about 0.2 to 70% by weight. Examples of the solid carrier or diluent are fine powders or granules of kaolin clay, attapulgite clay, bentonite, terra alba, pyrophyllite, talc, diatomaceous earth, calcite, walnut powders, urea, ammonium sulfate and synthetic hydrous silicate, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, N,N-dimethylformamide, acetonitrile, water, etc.

The surface active agent used for emulsification, dispersion or spreading may be of any type, for instance, either anionic or non-ionic. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the present invention are illustratively shown in the following examples wherein parts are by weight. The compound number of the active ingredient corresponds to the one in Table 2.

FORMULATION EXAMPLE 1

Fifty parts of Compound No. 1 or 2, 3 parts of calcium ligninsulfonate, 2 parts of sodium laurylsulfate and 45 parts of synthetic hydrous silicate are mixed well while being powdered to obtain a wettable powder.

FORMULATION EXAMPLE 2

Five parts of Compound No. 4 or 5, 14 parts of polyoxyethylenestyrylphenyl ether, 6 parts of calcium dodecylbenzenesulfonate, 30 parts of xylene and 45 parts of cyclohexanone are well mixed to obtain an emulsifiable concentrate.

FORMULATION EXAMPLE 3

One part of Compound No. 2, 6 or 11, 1 part of synthetic hydrous silicate, 2 parts of calcium ligninsulfonate, sulfonate, 30 parts of bentonite and 66 parts of kaolin clay are mixed well while being powdered. The mixture is then kneaded with water, granulated and dried to obtain granules.

FORMULATION EXAMPLE 4

Twenty-five parts of Compound No. 3 or 6 is mixed with 3 parts of polyoxyethylene sorbitan monooleate, 3 parts of carboxymethyl cellulose and 69 part of water and pulverized until the particle size of the mixture becomes less than 5 microns to obtain a suspension.

The benzothiazolones (I) thus formulated in any suitable preparation form are useful for the pre-emergence or post-emergence control of undesired weeds by soil or foliar treatment as well as flood fallowing treatment. These treatments include the application to the soil surface prior to or after the transplanting or the incorporation into the soil. The foliar treatment may be effected by spraying the herbicidal composition containing the benzothiazolones (I) over the top of the plants. It may also be applied directly to the weeds if care is taken to keep the chemical off the crop foliage.

The benzothiazolones (I) of the present invention may be used together with other herbicides to improve their activity as herbicides, and in some cases, a synergistic effect can be expected. Further, they may be applied in combination with insecticides, acaricides, nematocides, fungicides, plant growth regulators, fertilizers, soil improvers, etc.

Furthermore, the benzothiazolones (I) can be used as herbicides applicable to agricultural plowed fields as well as paddy fields. They are also useful as herbicides to be employed for orchards, pasture land, lawns, forests, non-agricultural fields, etc.

The dosage rate of the benzothiazolones (I) may vary depending on the prevailing weather conditions, the formulation used, the prevailing season, the mode of application, the soil involved, the crop and weed species, etc. Generally, however, the dosage rate is from 0.02 to 100 grams, preferably from 0.04 to 50 grams, of the active ingredient per are. The herbicidal composition of the invention formulated in the form of an emulsifiable concentrate, a wettable powder or a suspension may ordinarily be employed by diluting it with water at a volume of about 1 to 10 liters per are, if necessary, with addition of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition formulated in the form of granules may be normally applied as such without dilution.

The biological data of the benzothiazolones (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4 or 5, in which the numeral "0" indicates no material difference as seen in comparison with the untreated plant and the numeral "5" indicates the complete inhibition or death of the test plants.

The following compound was used for comparison.

| Compound No. | Chemical structure | Remarks |
|---|---|---|
| A | Cl, CH$_2$COOH, N, =O, S (benzothiazolinone structure) | Commercially available herbicide "benazolin" |

TEXT EXAMPLE 1

Cylindrical plastic pots (diameter, 10 cm; height 10 cm) were filled with upland field soil, and the seeds of Japanese millet, oats, tall morningglory and velvetleaf were sowed therein and covered with soil. A designated amount of the test compound formulated in an emulsifiable concentrate according to Formulation Example 2 was diluted with water, and the dilution was sprayed onto the soil surface by means of a small hand sprayer at a spray volume of 10 liters per are. The test plants were further grown in a greenhouse for 20 days, and the herbicidal activity was examined. The results are shown in Table 8.

TABLE 8

| | | Herbicidal activity | | | |
|---|---|---|---|---|---|
| Compound No. | Dosage (g/are) | Japanese millet | Oats | Tall morning-glory | Velvet-leaf |
| 1 | 20 | 5 | 5 | 5 | 5 |
| 2 | 20 | 5 | 5 | 5 | 5 |

TABLE 8-continued

| | | Herbicidal activity | | | |
|---|---|---|---|---|---|
| Compound No. | Dosage (g/are) | Japanese millet | Oats | Tall morning-glory | Velvet-leaf |
| | 5 | 4 | 4 | 4 | 5 |
| 3 | 20 | 5 | 4 | 5 | 5 |
| 5 | 20 | 5 | 5 | 5 | 5 |
| | 5 | 5 | 4 | 5 | 5 |
| 6 | 20 | 5 | 5 | 5 | 5 |
| | 5 | 5 | 4 | 5 | 5 |
| A | 20 | 2 | 0 | 3 | 4 |
| | 5 | 0 | 0 | 0 | 1 |

TEST EXAMPLE 2

Cylindrical plastic pots (diameter, 10 cm; height, 10 cm) were filled with upland field soil, and the seeds of Japanese millet and oats were sowed therein and cultivated in a greenhouse for 10 days. A designated amount of the test compound formulated in an emulsifiable concentrate according to Formulation Example 2 was diluted with water containing a spreading agent, and the dilution was sprayed over the foliage of the test plants by means of a small hand sprayer at a spray volume of 10 liters per are. The test plants were further grown in the greenhouse for 20 days, and the herbicidal activity was examined. The results are shown in Table 9.

TABLE 9

| Compound No. | Dosgae (g/are) | Herbicidal activity | |
|---|---|---|---|
| | | Japanese millet | Oats |
| 1 | 20 | 5 | 5 |
| 2 | 20 | 5 | — |
| 3 | 20 | 5 | 5 |
| 4 | 20 | 5 | 5 |
| 5 | 20 | 5 | 5 |
| 6 | 20 | 5 | 5 |
| 7 | 20 | 5 | 5 |
| 9 | 20 | 5 | 5 |
| 13 | 20 | 5 | — |
| A | 20 | 0 | 0 |

TEST EXAMPLE 3

Cylindrical plastic pots (diameter, 8 cm,; height, 12 cm) were filled with paddy field soil, and the seeds of barnyardgrass (*Echinochloa oryzicola*), broad-leaved weeds (i.e. common falsepimpernel, indian toothcup, waterwort) were sowed in 1 to 2 cm depth. Water was poured therein to make a flooded condition, and rice seedlings of the 2.5-leaf stage were transplanted therein, and the test plants were grown in a greenhouse. Six days (at that time weeds began to germinate) thereafter, a designated amount of the test compound formulated in an emulsifiable concentrate according to Formulation Example 2 and diluted with water (5 ml) was applied to the pots by perfusion. The test plants were grown for an additional 20 days in the greenhouse, and the herbicidal activity was examined. The results are shown in Table 10.

TABLE 10

| | | Herbicidal activity | | |
|---|---|---|---|---|
| Compound no. | Dosage (g/are) | Rice plant | Barnyard-grass | Broad-leaved weed |
| 1 | 0.63 | 0 | 5 | 5 |
| 2 | 0.63 | 1 | 5 | 5 |
| 3 | 0.63 | 0 | 5 | 5 |
| 4 | 0.63 | 0 | 5 | 5 |

TABLE 10-continued

| Compound no. | Dosage (g/are) | Herbicidal activity | | |
|---|---|---|---|---|
| | | Rice plant | Barnyard-grass | Broad-leaved weed |
| 5 | 0.63 | 0 | 5 | 5 |
| 8 | 0.63 | 0 | 5 | 5 |
| 10 | 0.63 | 0 | 5 | 5 |
| 11 | 0.63 | 0 | 5 | 5 |
| 13 | 0.63 | 0 | 5 | 5 |
| A | 0.63 | 0 | 1 | 0 |

TEST EXAMPLE 4

Vats (33 cm×23 cm×11 cm) were filled with upland field soil, and the seeds of soybean, cotton, tall morningglory, velvetleaf, black nightshade, barnyardgrass (*Echinochloa crus-galli*), johnsongrass and green foxtail were sowed therein to 1 to 2 cm depth. A designated amount of the test compound formulated in an emulsifiable concentrate according to Formulation Example 2 was diluted with water, and the dilution was sprayed onto the soil surface by means of a small hand sprayer at a spray volume of 10 liters per are. The test plants were further grown in a greenhouse for 20 days, and the herbicidal activity was examined. The results are shown in Table 11.

TABLE 11

| Compound No. | Dosage (g/are) | Herbicidal activity | | | | | | | |
|---|---|---|---|---|---|---|---|---|---|
| | | Soybean | Cotton | Tall morning-glory | Velvet-leaf | Black night-shade | Barnyard-grass | Johnson-grass | Green foxtail |
| 1 | 10 | — | 4 | 5 | 5 | 5 | 5 | 5 | 5 |
| 2 | 10 | — | 2 | 5 | 5 | 5 | 5 | 5 | 5 |
|   | 5  | — | 0 | 3 | 5 | 5 | 4 | 4 | 5 |
| 3 | 10 | 0 | 0 | — | 5 | 4 | 4 | 4 | 5 |
| 5 | 5  | — | 0 | 4 | 5 | 5 | 4 | 5 | 5 |
| 6 | 10 |   |   |   |   |   |   |   |   |
|   | 5  | — | 2 | 5 | 5 | 5 | 5 | 5 | 5 |
| 7 | 10 | — | — | — | 5 | 5 | 5 | 4 | 5 |
|   | 5  | 0 | 0 | — | 5 | 5 | 4 | 4 | 4 |
| A | 10 | 2 | 2 | 2 | 3 | 4 | 0 | 0 | 0 |
|   | 5  | 0 | 0 | 0 | 1 | 2 | 0 | 0 | 0 |

TEST EXAMPLE 5

Vats (33 cm×23 cm×11 cm) were filled with upland field soil, and the seeds of corn, tall morningglory, common cocklebur, velvetleaf and black nightshade were sowed therein and cultivated for 18 days in a greenhouse. A designated amount of the test compound formulated in an emulsifiable concentrate according to Formulation Example 2 was diluted with water containing a spreading agent, and the dilution was sprayed over the foliage of the test plants by means of a small hand sprayer at a spray volume of 5 liters per are. The test plants were further grown in the greenhouse for 20 days, and the herbicidal activity was examined. At the time of the application, the test plants were generally at the 1 to 4 leaf stage and in 2 to 12 cm height, although the growing stage of the test plants varied depending on their species. The results are shown in Table 12.

TABLE 12

| Compound No. | Dosage (g/are) | Herbicidal activity | | | | |
|---|---|---|---|---|---|---|
| | | Corn | Tall morning-glory | Common cocklebur | Velvet-leaf | Black night-shade |
| 2 | 0.63 | 1 | 5 | 4 | 5 | 5 |
| 4 | 0.63 | 2 | 5 | — | 5 | 5 |
| 5 | 0.63 | — | 5 | 4 | 5 | 5 |

TABLE 12-continued

| Compound No. | Dosage (g/are) | Herbicidal activity | | | | |
|---|---|---|---|---|---|---|
| | | Corn | Tall morning-glory | Common cocklebur | Velvet-leaf | Black night-shade |
| 6 | 0.63 | 2 | 5 | 5 | 5 | 5 |
| 7 | 0.63 | 2 | 5 | 4 | 5 | 4 |
| A | 0.63 | 0 | 0 | 0 | 1 | 1 |

TEST EXAMPLE 6

Wagner's pots (1/5000 are) were filled with paddy field soil, and the seeds of barnyardgrass (*Echinochloa oryzicola*), broad-leaved weeds (e.g. common falsepimpernel, indian toothcup, waterwort) and statoblast of needle spikerush were sowed in 1 to 2 cm depth. Water was poured therein to make a flooded condition. Rice seedlings of the 3-leaf stage were transplanted therein and grown in a greenhouse. Twelve days (at that time barnyardgrass began to germinate) thereafter, a designated amount of the test compound formulated in an emulsifiable concentrate according to Formulation Example 2 and diluted with water (10 ml) was applied to the pots by perfusion, followed by addition of water thereto to make a 4 cm depth. The test plants were grown for further 20 days in the greenhouse, and the herbicidal activity was examined. Two consecutive days after the treatment, water was leaked out in an amount of 3 cm depth per day. The results are shown in Table 33.

TABLE 13

| Compound No. | Dosage (g/are) | Herbicidal activity | | | |
|---|---|---|---|---|---|
| | | Rice plant | Barn-yard-grass | Broad-leaved weed | Needle spikerush |
| 1 | 1.25 | 1 | 4 | 5 | 4 |
| 2 | 1.25 | 1 | 4 | 5 | 4 |
| 5 | 1.25 | 1 | 5 | 5 | 4 |
| 6 | 1.25 | 1 | 5 | 5 | 5 |
| 9 | 1.25 | 1 | 4 | 5 | 4 |
| 10 | 2.5 | 1 | 4 | 5 | 4 |
| 11 | 1.25 | 1 | 5 | 5 | 3 |
| A | 2.5 | 0 | 0 | 1 | 0 |
|   | 1.25 | 0 | 0 | 0 | 0 |

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

What is claimed is:

1. A compound of the formula:

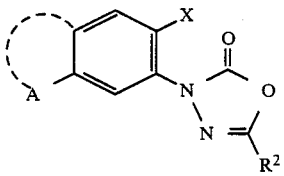

wherein A is a nitrogen-containing group selected from the group consisting of —N=C(NH$_2$)—S— and —NH—CO—S—, X is a fluorine atom or a chlorine atom and R$^2$ is a t-butyl group or a 1methylcyclopropyl group.

2. The compound according to claim 1, wherein A is a —N=C(NH$_2$)—S— group.

3. The compound according to claim 1, wherein A is a NH—CO—S— group.

4. The compound according to claim 1, wherein X is a fluorine atom.

5. The compound according to claim 1, wherein X is a chlorine atom.

6. The compound according to claim 1, wherein R$^2$ is a t-butyl group.

7. The compound according to claim 1, wherein R$^2$ is a 1-methylcyclopropyl group.

* * * * *